(12) United States Patent
Abehassera et al.

(10) Patent No.: US 10,139,380 B2
(45) Date of Patent: Nov. 27, 2018

(54) PREMISE OCCUPANCY DETECTION BASED ON CO2 GAS CONCENTRATION

(71) Applicants: Ilan Abehassera, New York, NY (US); Etienne Castanie, Tours (FR); Jocelyn Masserot, New York, NY (US); Dan Attali, New York, NY (US); Olivier Costier, New York, NY (US); Nellie Alimi, San Francisco, CA (US)

(72) Inventors: Ilan Abehassera, New York, NY (US); Etienne Castanie, Tours (FR); Jocelyn Masserot, New York, NY (US); Dan Attali, New York, NY (US); Olivier Costier, New York, NY (US); Nellie Alimi, San Francisco, CA (US)

(73) Assignee: Ilan Abehassera

( * ) Notice: Subject to any disclaimer, the term of this patent is extended or adjusted under 35 U.S.C. 154(b) by 859 days.

(21) Appl. No.: 14/610,964

(22) Filed: Jan. 30, 2015

(65) Prior Publication Data
US 2016/0223503 A1 Aug. 4, 2016

(51) Int. Cl.
*G01N 31/00* (2006.01)
*G01N 33/00* (2006.01)
*G06F 11/30* (2006.01)

(52) U.S. Cl.
CPC .......... *G01N 33/004* (2013.01); *Y02A 50/244* (2018.01)

(58) Field of Classification Search
CPC .................................................... G01N 33/004
See application file for complete search history.

(56) References Cited

U.S. PATENT DOCUMENTS

2013/0181617 A1* 7/2013 Maddox ............ H05B 37/0227
315/159

* cited by examiner

*Primary Examiner* — Phuong Huynh
(74) *Attorney, Agent, or Firm* — Farjam Majd

(57) ABSTRACT

A method and an apparatus are disclosed for detecting occupancy of a closed space based on Carbon Dioxide gas (CO2) concentration or change of such concentration. In various embodiments, a Base CO2 Concentration (BCC) may be measured to establish CO2 concentration in an empty closed space. An Average CO2 Concentration (ACC) may also be measured for a single average sized person. If at any time the Total CO2 Concentration (TCC) is measured to be higher than the sum of BCC and ACC, then it is determined that the presence of a person in the closed space is detected. In some embodiments, if TCC is measured to be more than BCC plus N times ACC, then it is determined that N people are present in the closed space, where N is an integer. Such determinations may be indicated by generating an alarm or alert.

19 Claims, 5 Drawing Sheets

PREMISE OCCUPANCY DETECTION BASED ON CO2 GAS CONCENTRATION

TECHNICAL FIELD

This application relates generally to occupancy detection in closed spaces. More specifically, this application relates to a method and apparatus for detecting the presence and/or the number of people or animals in a closed space based on CO2 gas emissions.

BRIEF DESCRIPTION OF THE DRAWINGS

The drawings, when considered in connection with the following description, are presented for the purpose of facilitating an understanding of the subject matter sought to be protected.

DETAILED DESCRIPTION

While the present disclosure is described with reference to several illustrative embodiments described herein, it should be clear that the present disclosure should not be limited to such embodiments. Therefore, the description of the embodiments provided herein is illustrative of the present disclosure and should not limit the scope of the disclosure as claimed. In addition, while the following description references detection of number of persons in a room, it will be appreciated that the disclosure may be applicable to counting animals in a closed enclosure, or people in a multiple-room building, and the like.

Briefly described, a method and an apparatus are disclosed for detecting occupancy of a closed space based on Carbon Dioxide gas (CO2) concentration or change of such concentration. In various embodiments, a Base CO2 Concentration (BCC) may be measured to establish CO2 concentration in an empty closed space. An Average CO2 Concentration (ACC) may also be measured for a single average sized person. If at any time the Total CO2 Concentration (TCC) is measured to be higher than the sum of BCC and ACC, then it is determined that the presence of a person in the closed space is detected. In some embodiments, if TCC is measured to be more than BCC plus N times ACC, then it is determined that N people are present in the closed space, where N is an integer. Such determinations may be indicated by generating an alarm or alert. Detection of occupancy may be useful in many applications such as space monitoring in schools or other buildings, fire evacuation, car occupancy detection, burglary detection, security purposes, detection of unauthorized presence, triggering cameras in a space to start recording events, calling security staff, space preparation (turning on lights, heat, etc.), space overflow estimation, and other applications.

Facilities and building monitoring and control is an important element of facilities management. Many techniques are used to monitor facilities such as cameras, motion detectors, light sensors, and the like. However, each of these techniques have some shortcomings in various situations. For example, motion detectors only detect motion. A person hidden from the line of sight of such devices can easily elude them. Similarly, detection by cameras can be circumvented in various ways, especially if they are not being monitored by someone. Therefore, there is a need for a technique of detection that can overcome these difficulties and provide additional detection capabilities, such as estimating the total number of people or animals in a closed space, in a non-intrusive, cost-effective, and reliable manner.

Figure 1A:
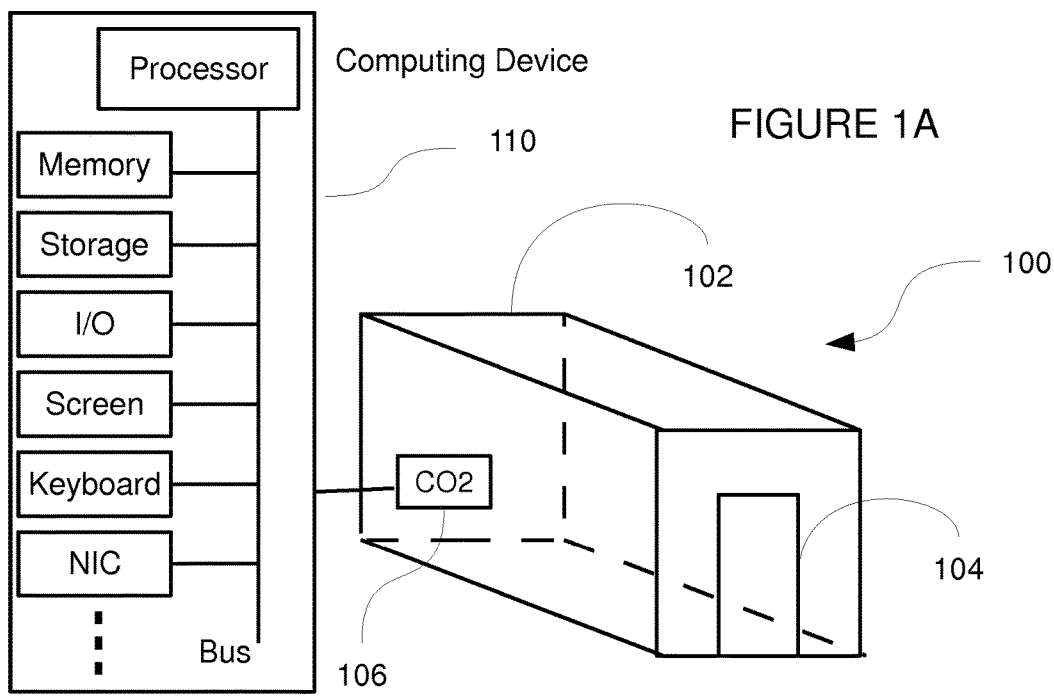
FIG. 1A shows an example empty closed space with a CO2 measurement device.

FIG. 1A shows an example empty closed space with a CO2 measurement device. In various embodiments, an empty closed space CO2 detection system 100 may include a building or enclosure not exposed to open air 102 having points of entrance and exit 104, and a CO2 detection and/or measurement device 106 coupled with a computing device 110.

In various embodiments, the CO2 measurement device 106 may be coupled, by wire or wirelessly, to an electronic controller that is configured to calculate BCC, ACC, and TCC during regular intervals or based on an event, such as a change in CO2 concentration.

In some embodiments, the CO2 detection device may include one or multiple devices deployed at various locations within the target space, each coupled with one or more computing devices. The computing device may combine the data from the multiple CO2 detection devices based on a predetermined algorithm, such as averaging the corresponding data from all the CO2 detection devices, applying a voting algorithm to select the data item most closely supported by the data from the highest number of CO2 detection devices, and the like.

The computing device 110 may be local or remote, and may include one or several computers. In various embodiments, the electronic controller may be hardware controller, a software controller running on a computer system, such as a Personal Computer (PC), a combination of hardware and software, or other similar computing devices.

Those skilled in the art will appreciate that digital computing devices, such as computing device 110, generally include one or more programmable processors; memory modules such as RAM (Random Access Memory) and/or ROM (Read Only Memory); storage devices, such as a magnetic disk, optical disk, non-volatile memory like Flash, and the like; Input/Output (I/O) interface for printers, scanners, measurement devices like the CO2 measurement device, and the like; input interfaces such as keyboard and touchpad interfaces; output interfaces such as display screen, touch screens and multi-touch screens; Network Interface Card (NIC) for wired or wireless communications such as WiFi, BlueTooth, and the like; an operating system software residing in and loaded from ROM and/or from a storage device, executed on the processor to control the basic functions of the PC like file and I/O management;

application software, loaded from a storage device, designed for performing specific tasks such as word processing, email, device control and management, and the like; and other hardware and software components as needed.

In various embodiment, the empty space does not include any living creatures, human or animal and is relatively non-exposed to open air. As such, a base level of CO2 concentration may be detected in such a space that is substantially constant over time, barring entry by living humans or animals. CO2 is a naturally occurring gas with an average concentration of about 400 ppm (parts per million) by volume in the open air (or about 591 ppm by mass). A closed space may have a different concentration of CO2 because of various processes, plants, air conditioning and handling equipment, air filters, industrial activities in the close vicinity, seasonal changes, and the like. However, for an empty space in a particular place with particular equipment, environment, and conditions, the CO2 concentration is generally relatively stable and static over extended periods of time such as a few hours, days, or weeks and may fluctuate slowly over longer periods.

Figure 1B:
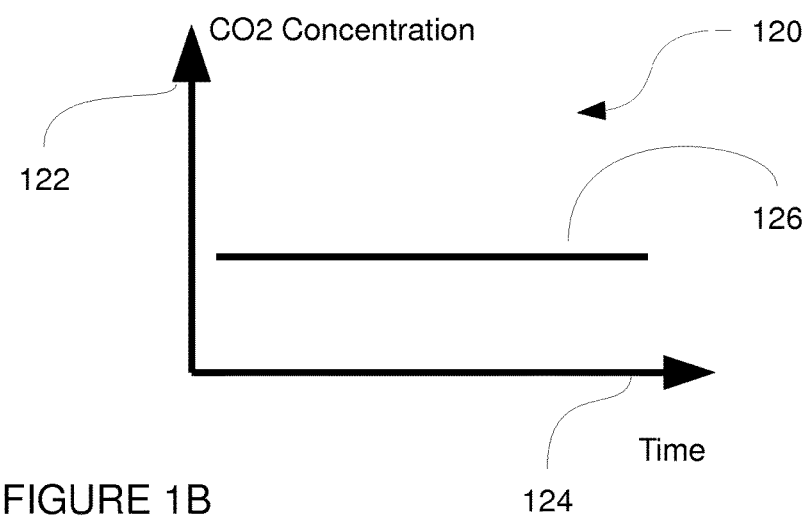
FIG. 1B shows an example Base CO2 Concentration (BCC) curve corresponding to the approximately constant CO2 concentration in the empty closed space of FIG. 1A.

FIG. 1B shows an example Base CO2 Concentration (BCC) curve corresponding to the approximately constant CO2 concentration in the empty closed space of FIG. 1A. In various embodiments, the CO2 concentration is shown on the vertical (or dependent) axis 122 of the Cartesian reference frame 120 with time shown on the horizontal (or independent) axis 124, and the BCC curve 126 depicts the changes in CO2 concentration over time, which is substantially constant for an empty space over certain time frames. Of course, this constant CO2 level, or BCC, may vary from one space to another and has to be determined separately for each space. In some embodiments, the BCC for a given space may be updated periodically, for example, every night or weekend, when occupants are known not to be in the target space.

Figure 2A:
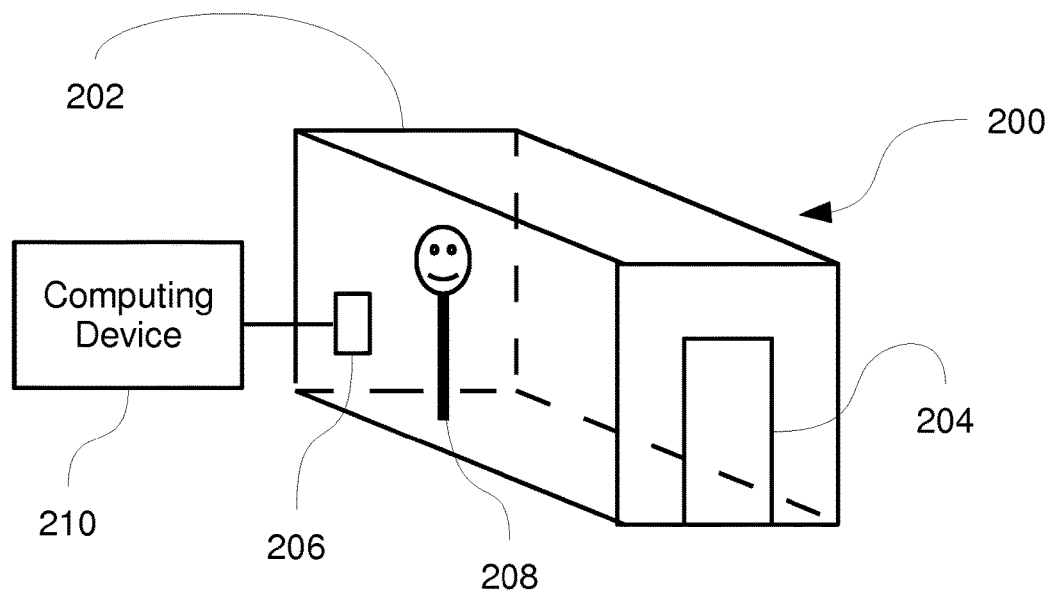
FIG. 2A shows the example closed space of FIG. 1A with one occupant.

FIG. 2A shows the example closed space of FIG. 1A with one occupant. In various embodiments, closed space CO2 detection system 200 may include a building or enclosure not exposed to open air 202 having points of entrance and exit 204, a CO2 detection and/or measurement device 206 coupled with a computing device 210, and one occupant 208.

In various embodiments, when occupant 208 enters the building 202, the average CO2 concentration starts to rise. The CO2 measurement device 206 detects the change in CO2 concentration and transmits the information to the controller or computing device 210 for processing. The computing device may maintain a running log or database of CO2 concentration data and add any newly transmitted information to the database. The computing device may perform any kind of processing and computation on the data such as statistical analysis, threshold calculations, estimation of number of occupants, time-stamping various events such as points when CO2 concentration rises or falls, issuing alarms or notifications for unauthorized access to a space to police or security personnel, controlling other devices such as opening or closing vents, starting or shutting off air handling systems like air conditions, and the like. Detection of occupancy may be useful in many applications such as space monitoring in schools or other buildings, fire evacuation, car occupancy detection, burglary detection, security purposes, detection of unauthorized presence, triggering cameras in a space to start recording events, calling security staff, space preparation (turning on lights, heat, etc.), space overflow estimation, and other applications.

In various embodiments, the CO2 measurement device 206 and/or computing device 210 may be deployed in spaces other than buildings, such as cars, ships, submarines, aircraft, and any other enclosed space that has controlled or limited access to and interchange with open air. For example, CO2 detector may be used to detect the occupancy in a car to prevent theft or other unauthorized access to the vehicle. This may be as an independent security system or as a supplement to other security systems. Such detection system may also be used to trigger various actions such as turning on a video or still image camera to take pictures after the detection of a occupant. It may also issue a warning that the occupancy capacity of the space, building or vehicle, is likely exceeded based on average CO2 concentration.

In various embodiments, the CO2 detection system 200 may compute various quantities to compare to a predetermined threshold and take a predetermined action as a result. In various embodiments, BCC may be measured to establish CO2 concentration in an empty closed space. An ACC may also be measured for a single average sized person. If at any time TCC is measured or calculated to be higher than the sum of BCC and ACC, then it is determined that the presence of at least one person in the closed space is detected. In some embodiments, if TCC is measured to be more than BCC plus N times ACC, then it may be determined that approximately N people are present in the closed space, where N is an integer.

Those skilled in the art will appreciate that ACC, being a concentration, depends on the size of the target space. A particular person (or animal) has a particular CO2 emission per minute. This particular rate of emission of CO2 will result in a different CO2 concentration in a small room versus a big hall. The rate of CO2 emission starts accumulating in a space until the CO2 concentration in the space reaches a steady state in equilibrium with air circulation through the space. Therefore, the ACC for a given target closed space may be calculated based on the ratio of volume or mass of CO2 with respect to the volume or mass of air inside the target space. Hence, a living creature produces a certain ACC within a certain closed space, that is generally different form the ACC produced by the same creature in a different closed space. Such data may be measured directly by the CO2 measurement device 206, or be calculated by the computing device 210 based on CO2 emission rate for the type of creature (person or animal) and the size of the target space.

ACC may be calculated as follows:

$$ACC=(\text{Vol. or mass of CO2})/(\text{Vol. or mass of air}); \quad \text{Equation (1)}$$

The integer N may be calculated as follows:

$$N=(TCC-BCC)/ACC; \quad \text{Equation (2)}$$

In the general case, precise calculation of N may not be possible due to the variation in the CO2 emissions of people of various sizes, ages, and sexes. However, depending on the use of the building or enclosure, different ACC may be obtained to more accurately represent the average occupant. For example, if this CO2 detection system is deployed in a kindergarten setting, where small children attend, the ACC for an average child of that age may be obtained and used to calculate N more accurately.

Those skilled in the art will appreciate that the same techniques as described above may be applied to enclosures that hold animals, such as live stock, in a substantially similar manner.

Figure 2B:
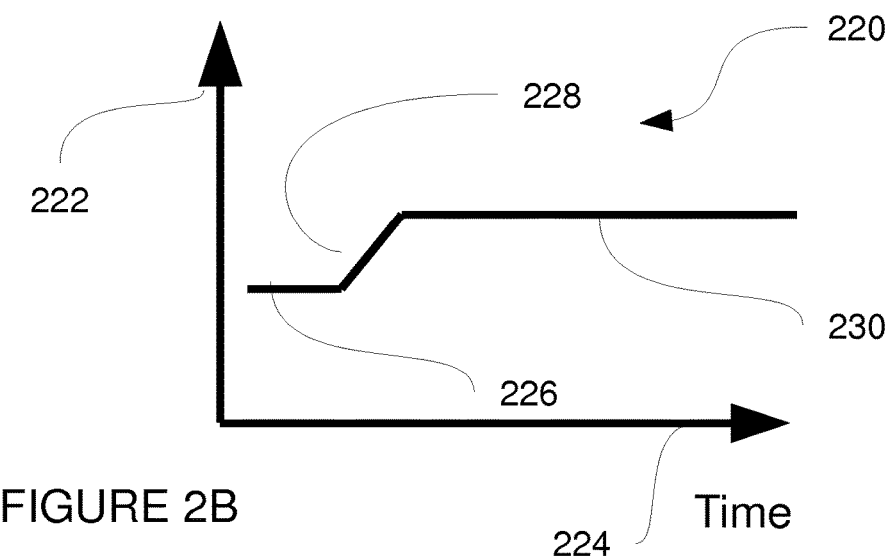
FIG. 2B shows an example CO2 concentration curve corresponding to the CO2 concentration in the closed space of FIG. 2A with one occupant.

FIG. 2B shows an example CO2 concentration curve corresponding to the CO2 concentration in the closed space of FIG. 2A with one occupant. In various embodiments, the CO2 concentration is shown on the vertical (or dependent) axis 222 of the Cartesian reference frame 220 with time shown on the horizontal (or independent) axis 224, and the CO2 concentration curve depicts the changes in CO2 concentration over time as a function of the number of occupant in the space 202. This curve includes several distinct sections including the BCC section 226, a BCC to a single occupant transition curve 228, and the TCC with a single occupant 230.

In various embodiments, BCC segment 226 represents the CO2 concentration level in the empty space. When occupant 208 enters the space, the CO2 concentration level starts rising over time, as represented by the transition segment 228. After some time passes, the length of which depends chiefly on the size of the space and the occupant, the CO2 concentration level starts leveling off and stabilizing to the TCC level as represented by segment 230. Based on this data, the computing device 210 can determine that an occupant has entered the space. At this time, the computing device may take various actions as described above with respect to FIGS. 1A and 2A.

Figure 3A:
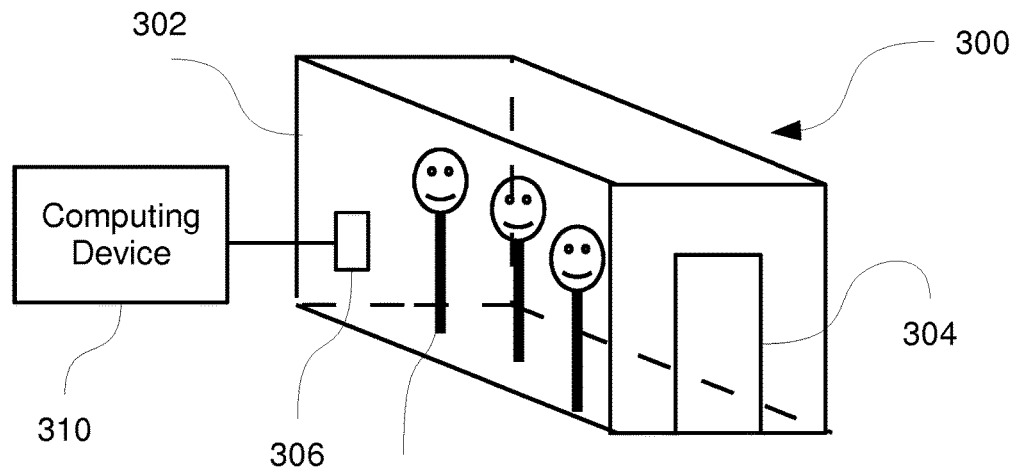
FIG. 3A shows the example closed space of FIG. 1A with more than one occupant.

FIG. 3A shows the example closed space of FIG. 1A with more than one occupant. In various embodiments, closed space CO2 detection system 300 may include a building or enclosure not exposed to open air 302 having points of entrance and exit 304, a CO2 detection and/or measurement device 306 coupled with a computing device 310, and several occupants 308.

In various embodiments, In various embodiments, when several additional occupants 308 enter the building 302, the average CO2 concentration starts to rise further. The CO2 measurement device 306 detects the change in CO2 concentration and transmits the information to the controller or computing device 310 for processing. The computing device may update the running log or database of CO2 concentration data and add any newly transmitted information to the database. The computing device may perform any kind of processing and computation on the new data such as those described above with respect to FIG. 2A and elsewhere in this specification.

Figure 3B:
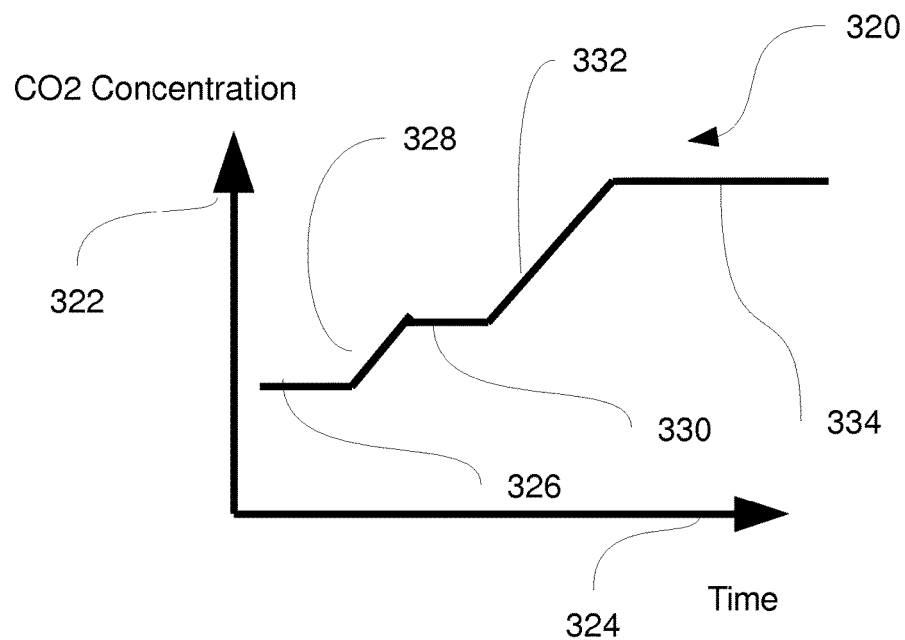
FIG. 3B shows an example CO2 concentration curve corresponding to the CO2 concentration in the closed space of FIG. 3A with more than one occupant.

FIG. 3B shows an example CO2 concentration curve corresponding to the CO2 concentration in the closed space of FIG. 3A with more than one occupant. In various embodiments, the CO2 concentration is shown on the vertical (or dependent) axis 322 of the Cartesian reference frame 320 with time shown on the horizontal (or independent) axis 324, and the CO2 concentration curve depicts the changes in CO2 concentration over time as a function of the number of occupant in the space 302. This curve includes several distinct segments or sections including the BCC section 326, a BCC to a single occupant first transition curve 328, a first TCC with a single occupant 330, a second transition curve 332 from the first TCC 330 to a second TCC 334, and the second TCC 334 with several occupants.

In various embodiments, BCC segment 326 represents the CO2 concentration level in the empty space. When additional occupants 308 (in addition to the first occupant 208 of FIG. 2A) enter the space, the CO2 concentration level starts rising further over time, as represented by the transition segment 332. After some time passes, the length of which depends chiefly on the size of the space and the occupant, the CO2 concentration level starts leveling off and stabilizing to the new TCC level as represented by segment 334. Based on this data, the computing device 310 can determine that more occupants have entered the space and calculate their approximate number. At this time, the computing device may take various other actions as described above with respect to FIGS. 1A and 2A.

Figure 4A:
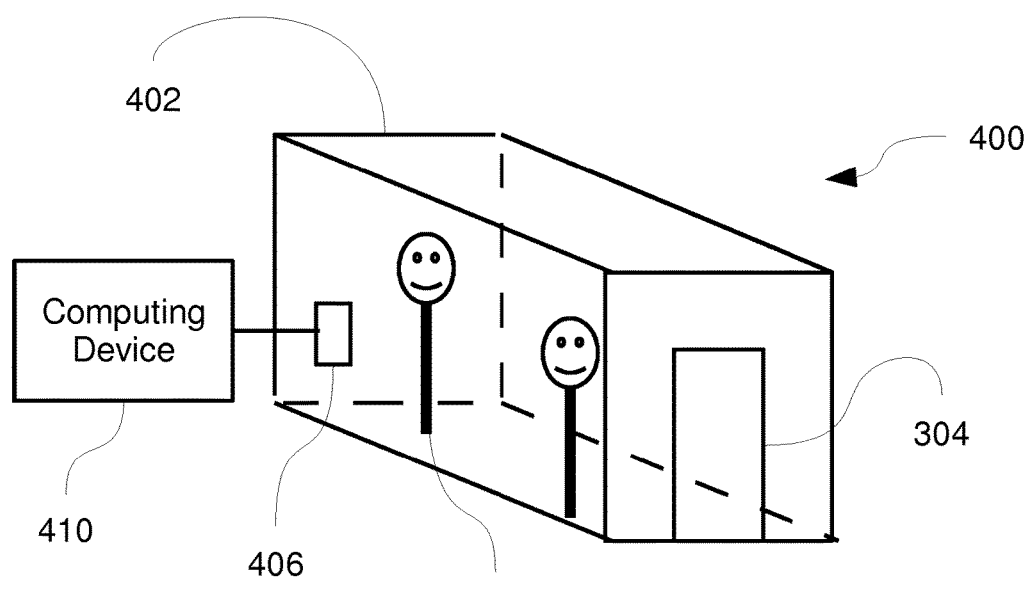
FIG. 4A shows the example closed space of FIG. 3A with fewer occupants.

FIG. 4A shows the example closed space of FIG. 3A with fewer occupants. In various embodiments, closed space CO2 detection system 300 may include a building or enclosure not exposed to open air 402 having points of entrance and exit 404, a CO2 detection and/or measurement device 406 coupled with a computing device 410, and several occupants 408, one or more less than the occupants shown in FIG. 3A.

In various embodiments, In various embodiments, when several occupants 408 leave the building 302, the average CO2 concentration starts to fall. The CO2 measurement device 406 detects the change in CO2 concentration and transmits the information to the controller or computing device 410 for processing. The computing device may update the running log or database of CO2 concentration data and add any newly transmitted information to the database. The computing device may perform any kind of processing and computation on the new data such as those described above with respect to FIG. 2A and elsewhere in this specification.

Figure 4B:
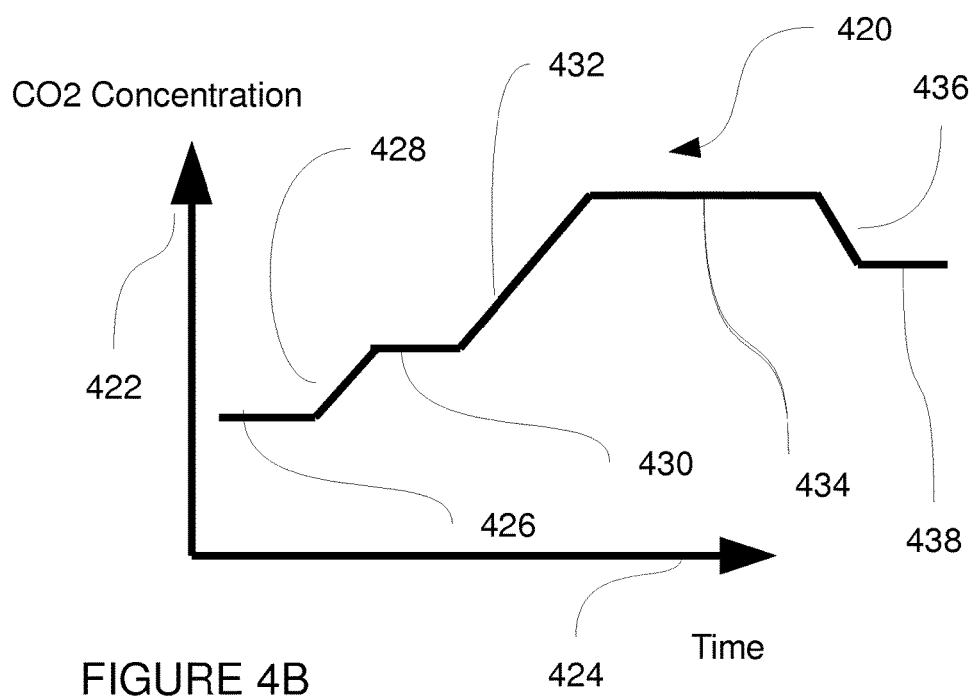
FIG. 4B shows an example CO2 concentration curve corresponding to the CO2 concentration in the closed space of FIG. 4A with fewer occupants.

In various embodiments, as people enter and exit the space or building 402, the computing device 410 may track the rise and fall of the CO2 concentration in the space in terms of CO2 concentration versus time data, which is suitable to construct a curve similar to those shown in FIGS. 2B, 3B, and 4B.

FIG. 4B shows an example CO2 concentration curve corresponding to the CO2 concentration in the closed space of FIG. 4A with fewer occupants. In various embodiments, the CO2 concentration is shown on the vertical (or dependent) axis 422 of the Cartesian reference frame 420 with time shown on the horizontal (or independent) axis 424, and the CO2 concentration curve depicts the changes in CO2 concentration over time as a function of the number of occupant in the space 402. This curve includes several distinct segments or sections including the BCC section 426, a BCC to a single occupant first transition curve 428, a first TCC with a single occupant 430, a second transition curve 432 from the first TCC 430 to a second TCC 434, the second TCC 434 with several occupants. a third transition curve 436 from the second TCC 434 to a fourth TCC 438, and the fourth TCC 438, reflecting the reduced CO2 concentration after one or more occupants have left the space.

Figure 5:
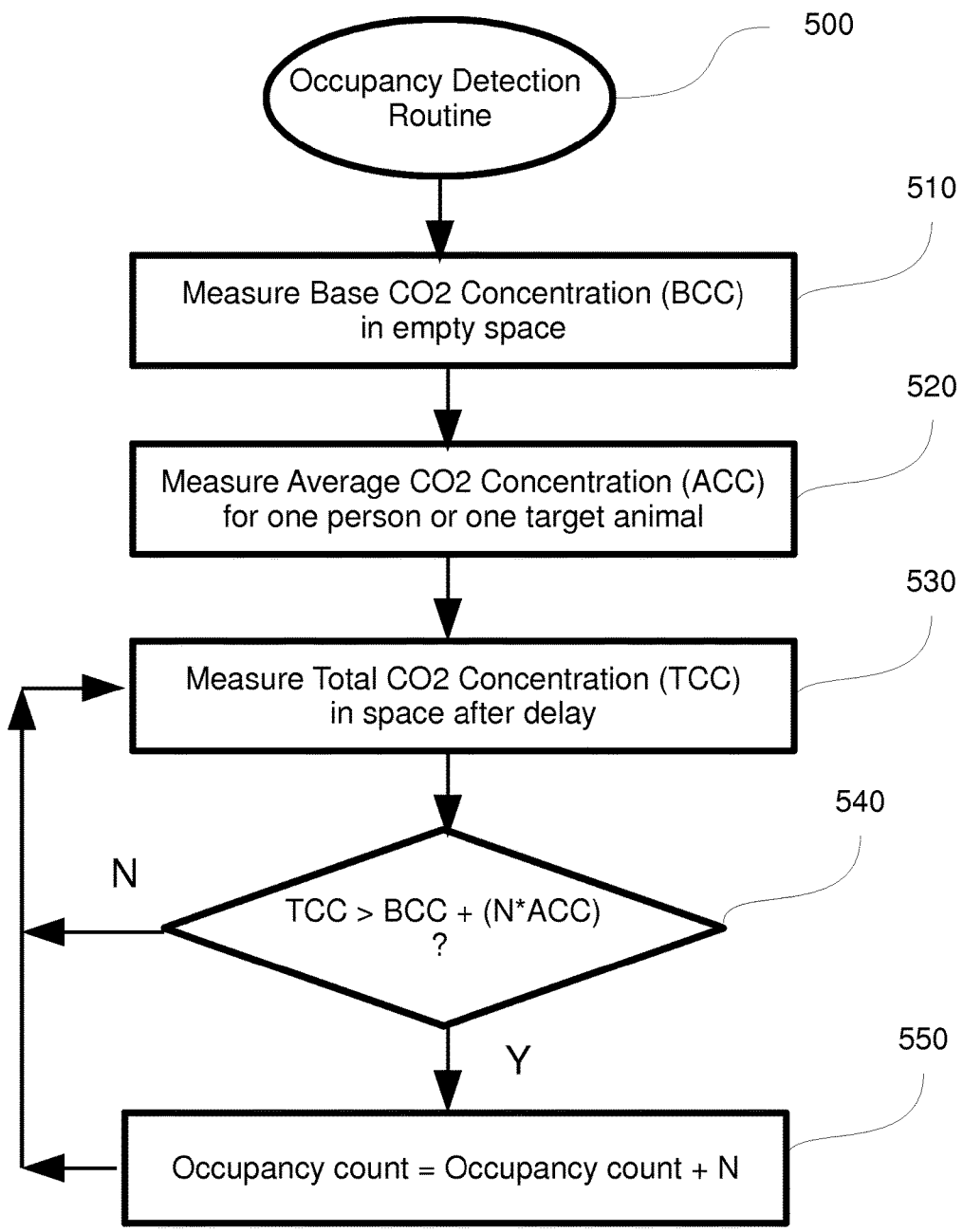
FIG. 5 shows an example flow diagram for the process of approximating the number of occupants in a closed space by detecting CO2 concentration.

FIG. 5 shows an example flow diagram for the process of approximating the number of occupants in a closed space by detecting CO2 concentration. An occupancy detection routine starts at block 500 and proceeds to block 510.

At block 510 the BCC for an empty space may be measured by the CO2 measurement device by taking one or more samples over an extended period of time, such as a few hours. The BCC for every space may be different. It may also be different at different times and seasons. Hence several versions of BCC may be measured and maintained in the database for future use. A single BCC may also be calculated by calculating various statistical averages, such as mean, mode, and median, or by other algorithms such as a voting algorithm either over time (samples from the same CO2 measurement device at different times) or space (samples from several CO2 measurement devices at the same time.) The routine proceeds to block 520.

At block 520, an average CO2 concentration (ACC) is measured, calculated, or obtained from a third party database for a single type of person (various sizes, sexes, ages, etc.) or type of animal (for example, cow, sheep, chicken, etc.) to be used later for detection of occupancy or approximating the number of occupants in a given space. proceed to block 530.

At block 530, measure or calculate total CO2 concentration (TCC) in the target space. TCC may be measured and updated periodically based on one or more samples. Proceed to decision block 540.

At block 540, compare TCC with BCC to ascertain if anybody has entered the space. If TCC exceeds BCC by at least one unit of ACC for the target space, then it may be determined that at least one person has entered the space. If TCC exceed BCC by multiple units (N units) of ACC, then the number of people may be estimated according to Equation (2) above. Calculate N. Other actions may be taken at this time, as described above with respect to FIGS. 2, 3, and 4. If TCC does not exceed BCC by N times ACC (where N can be 1 or a larger integer), then proceed back to block 530. If TCC exceeds BC by N times ACC, then proceed to block 550.

At block 550, add N to an Occupancy Count counter and proceed back to block 530 to repeat the process and continually monitor or track the space for fluctuations in CO2 concentration.

It will be understood that each block of the flowchart illustration, and combinations of blocks in the flowchart illustration, can be implemented by computer program instructions. These program instructions may be provided to a processor to produce a machine, such that the instructions, which execute on the processor, create means for implementing the actions specified in the flowchart block or blocks. The computer program instructions may be executed by a processor to cause a series of operational steps to be performed by the processor to produce a computer implemented process such that the instructions, which execute on the processor to provide steps for implementing the actions specified in the flowchart block or blocks. The computer program instructions may also cause at least some of the operational steps shown in the blocks of the flowchart to be performed in parallel. Moreover, some of the steps may also be performed across more than one processor, such as might arise in a multi-processor computer system. In addition, one or more blocks or combinations of blocks in the flowchart illustration may also be performed concurrently with other blocks or combinations of blocks, or even in a different sequence than illustrated without departing from the scope or spirit of the disclosure.

Accordingly, blocks of the flowchart illustration support combinations of means for performing the specified actions, combinations of steps for performing the specified actions and program instruction means for performing the specified actions. It will also be understood that each block of the flowchart illustration, and combinations of blocks in the flowchart illustration, can be implemented by special purpose hardware based systems which perform the specified actions or steps, or combinations of special purpose hardware and computer instructions.

It will be further understood that unless explicitly stated or specified, the steps described in a process are not ordered and may not necessarily be performed or occur in the order described or depicted. For example, a step A in a process described prior to a step B in the same process, may actually be performed after step B. In other words, a collection of steps in a process for achieving an end-result may occur in any order unless otherwise stated.

Changes can be made to the claimed invention in light of the above Detailed Description. While the above description details certain embodiments of the invention and describes the best mode contemplated, no matter how detailed the above appears in text, the claimed invention can be practiced in many ways. Details of the system may vary considerably in its implementation details, while still being encompassed by the claimed invention disclosed herein.

Particular terminology used when describing certain features or aspects of the invention should not be taken to imply that the terminology is being redefined herein to be restricted to any specific characteristics, features, or aspects of the invention with which that terminology is associated. In general, the terms used in the following claims should not be construed to limit the claimed invention to the specific embodiments disclosed in the specification, unless the above Detailed Description section explicitly defines such terms. Accordingly, the actual scope of the claimed invention encompasses not only the disclosed embodiments, but also all equivalent ways of practicing or implementing the claimed invention.

The above specification, examples, and data provide a complete description of the manufacture and use of the composition of the invention. Since many embodiments of the invention can be made without departing from the spirit and scope of the invention, the invention resides in the claims hereinafter appended. It is further understood that this disclosure is not limited to the disclosed embodiments, but is intended to cover various arrangements included within the spirit and scope of the broadest interpretation so as to encompass all such modifications and equivalent arrangements.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

While the present disclosure has been described in connection with what is considered the most practical and preferred embodiment, it is understood that this disclosure is not limited to the disclosed embodiments, but is intended to cover various arrangements included within the spirit and scope of the broadest interpretation so as to encompass all such modifications and equivalent arrangements.

What is claimed is:

1. A system for detecting occupancy in a target space, the system comprising:
    a target closed space with limited exposure to open air;
    a $CO_2$ measurement device deployed within the target closed space;
    a computing device coupled with the $CO_2$ measurement device, and configured to calculate a Base $CO_2$ Concentration (BCC) in the target closed space, an Average $CO_2$ Concentration (ACC) produced by a living creature in the target closed space, and a Total $CO_2$ Concentration (TCC) in the target closed space, based on $CO_2$ measurement data collected by the $CO_2$ measurement device; and
    wherein the system for detecting occupancy determines occupancy by whether TCC exceeds a sum of BCC and ACC.

2. The system of claim 1, wherein the BCC is measured periodically.

3. The system of claim 1, wherein the BCC is calculated based on a statistical average including a mean, a mode, and a median of several measured $CO_2$ concentration data.

4. The system of claim 1, wherein the ACC is measured directly in the target closed space by the $CO_2$ measurement device.

5. The system of claim 1, wherein ACC is calculated based on data from a third party source about the emission rate of the living creature and the size of the target closed space.

6. The system of claim 1, wherein the computing device is further configured to take an action including one or more of issuing an alarm, recording occupancy $CO_2$ data with timestamp of events in a database, and generating a $CO_2$ concentration curve versus time.

7. The system of claim 1, wherein the computing device is further configured to control other devices associated with the target closed space, including turning on a video camera, turning on or off an air conditioning unit, and controlling other air handling equipment.

8. The system of claim 1, wherein the computing device is further configured to detect the entry or exit of an occupant from the target closed space.

9. The system of claim 1, wherein the computing device is further configured to estimate the number of occupants at a particular time in the target closed space.

10. A method of detecting occupancy in a target space, the method comprising:
    measuring $CO_2$ concentration in a closed target space;
    transmitting data resulting from measurements of $CO_2$ concentration to a computing device;
    computing a Base $CO_2$ Concentration (BCC) in the target closed space, an Average $CO_2$ Concentration (ACC) produced by a living creature in the target closed space, and a Total $CO_2$ Concentration (TCC) in the target closed space, based on $CO_2$ measurement data transmitted by the $CO_2$ measurement device; and
    detecting occupancy of the target closed space by determining whether TCC exceeds the sum of BCC and ACC.

11. The method of claim 10, further comprising estimating a number of occupants of the target closed space by determining whether TCC exceeds the sum of BCC and N times ACC, wherein N is an integer and is an estimate of the number of the occupants.

12. The method of claim 10, further comprising issuing an alarm if it is determined that TCC exceeds the sum of BCC and ACC.

13. The method of claim 10, further comprising controlling other devices associated with the target closed space, including turning on a video camera, turning on or off an air conditioning unit, and controlling other air handling equipment.

14. The method of claim 10, wherein measuring $CO_2$ concentration comprises measuring $CO_2$ concentration by multiple $CO_2$ measurement devices deployed within the target closed space.

15. The method of claim 10, wherein transmitting data comprises wireless transmission of data to the computing device.

16. A method of estimating a number occupants in a target space, the method comprising:
    measuring $CO_2$ concentration in a closed target space;
    transmitting data resulting from measurements of $CO_2$ concentration to a computing device;
    computing a Base $CO_2$ Concentration (BCC) in the target closed space, an Average $CO_2$ Concentration (ACC) produced by a living creature in the target closed space, and a Total $CO_2$ Concentration (TCC) in the target closed space, based on $CO_2$ measurement data transmitted by the $CO_2$ measurement device; and
    estimating a number N of occupants if TCC exceeds the sum of BCC and N times ACC, wherein N is an integer.

17. The method of claim 16, further comprising issuing an alarm if it is determined that TCC exceeds the sum of BCC and ACC.

18. The method of claim 16, further comprising controlling other devices associated with the target closed space, including turning on a video camera, turning on or off an air conditioning unit, and controlling other air handling equipment.

19. The method of claim 16, wherein measuring $CO_2$ concentration comprises measuring $CO_2$ concentration periodically.

* * * * *